(12) United States Patent
Grosse et al.

(10) Patent No.: US 7,501,519 B2
(45) Date of Patent: *Mar. 10, 2009

(54) METHOD FOR PRODUCING BIPERIDEN IV

(75) Inventors: Markus Grosse, Schwetzingen (DE);
Klaus Martin Weber, Ludwigshafen (DE); Marco Thyes, Ludwigshafen (DE); Peter Klein, Birkenheide (DE); Elmar Vilsmaier, Otterbach (DE)

(73) Assignee: Abbott GmbH & Co., KG, Wiesbaden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/478,384

(22) PCT Filed: May 17, 2002

(86) PCT No.: PCT/EP02/05497

§ 371 (c)(1),
(2), (4) Date: May 3, 2004

(87) PCT Pub. No.: WO02/096874

PCT Pub. Date: Dec. 5, 2002

(65) Prior Publication Data

US 2004/0186294 A1    Sep. 23, 2004

(30) Foreign Application Priority Data

May 18, 2001    (DE) ................... 101 24 453

(51) Int. Cl.
*C07D 211/06*    (2006.01)
(52) U.S. Cl. ................................. 546/205
(58) Field of Classification Search ................... 546/205
See application file for complete search history.

(56) References Cited

U.S. PATENT DOCUMENTS 2,789,110 A * 4/1957 Klavehn .................... 546/205
6,835,839 B2 * 12/2004 Klein et al. ................ 546/205

FOREIGN PATENT DOCUMENTS

DE        1 005 067         3/1957
WO    WO 02/096874 A2     12/2002

OTHER PUBLICATIONS

Caplus English Abstract. Enantioselective total synthesis of (-)-preclavulone-A E.J. Corey et al 1988. vol. 29 Issue 9, pp. 995-998.*
Aldolisation . . . R. Bloch et al Tetrahedron vol. 44, issue 9 1988 pp. 2523-2539.*
Bloch R et al, 1988, Aldolisation stereocontrolee par un groupe thermolabile synthese steroselective de composes possedant trois carbones asymetriques consecutifs.*
Diels-Alder Reaction chemhelper.com—2008 pp. 1-4.*
Dunwiddie 1965 J. Org. Chem. 1965.*
Manfrid Eltze, et al., Affinity and selectivity of biperiden enantiomers for muscarinic receptor subtypes, European Journal of Pharmacology, 1998, 11-19, vol. 158, Germany.
E. J. Corey, et al., Enantioselective Total Synthesis of (-)-Preclavulone-A, Tetrahedron Letters, 1988, 995-998, vol. 29, No. 9, Great Britain.

* cited by examiner

*Primary Examiner*—Rita J Desai
(74) *Attorney, Agent, or Firm*—Dykema Gossett PLLC

(57) ABSTRACT

The invention relates to a method for producing biperiden by reacting exo-1-(bi-cyclo[2.2.1]hept-5-en-2-yl)-3-piperidino-1-propanone with a phenylmagnesium compound. According to the invention, exo-1-(bi-cyclo[2.2.1]hept-5-en-2-yl)-3-piperidino-1-propanone can be obtained by reacting the exo-ether of enol silylene of formula (IV) with a compound of N-methylenepiperidinium.

17 Claims, No Drawings

METHOD FOR PRODUCING BIPERIDEN IV

CROSS-REFERENCE TO RELATED APPLICATION

This application is a Section 371 National Stage Application of application No. PCT/EP02/05497 filed on May 17, 2002.

The present invention relates to a method for producing biperiden.

Biperiden is a well-known central anticholinergic agent and is employed for the treatment of Parkinson's disease (Ullmanns Enzyklopädie der technischen Chemie, 4the edition, volume 21, Verlag Chemie, 1982, p. 627). It comprises a racemate of 1-(bicyclo[2.2.1]hept-5-en-2-yl(exo,R))-1-phenyl-3-piperidino-propanol(1,S) and 1-(bicyclo[2.2.1]hept-5-en-2-yl(exo,S))-1-phenyl-3-piperidinopropanol(1,R) (Ia) and represents one of four possible pairs of enantiomers (Ia-d) of the amino alcohol 1-(bicyclo[2.2.1]hept-5-en-2-yl)-1-phenyl-3-piperidino-1-propanol (I).

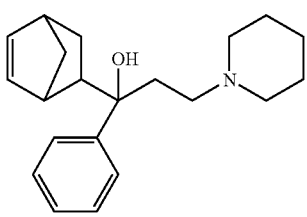

(I)

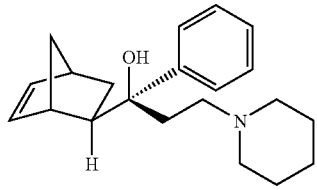

(Ia)

(exo, R)/(1, S)

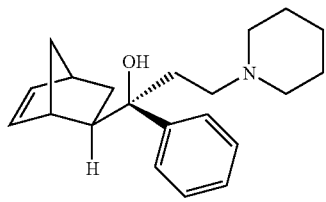

(exo, S)/(1, R)

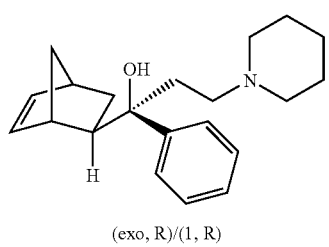

(Ib)

(exo, R)/(1, R)

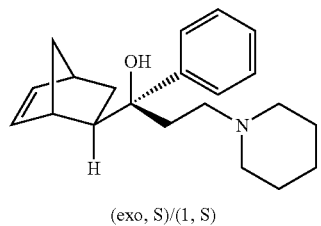

(exo, S)/(1, S)

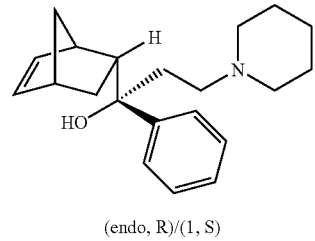

(Ic)

(endo, R)/(1, S)

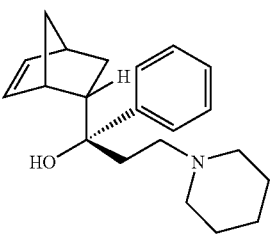

(endo, S)/1, R)

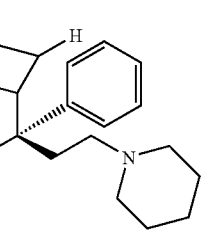

(Id)

(endo, R)/(1, R)

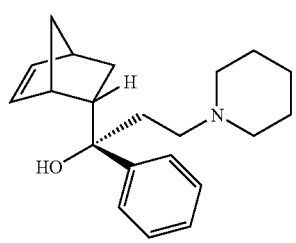

(endo, S)/(1, S)

DE 1 005 067 and U.S. Pat. No. 2,789,110 describe the preparation of the amino alcohol I by reacting 1-(bicyclo[2.2.1]hept-5-en-2-yl)-3-piperidino-1-propanone (II) with a phenylmagnesium halide. U.S. Pat. No. 2,789,110 additionally describes the preparation of the propanone II starting from 1-(bicyclo[2.2.1]hept-5-en-2-yl)-ethanone (III), paraformaldehyde and piperidine hydrochloride in a Mannich reaction, and the preparation of the ethanone III from cyclopentadiene and methyl vinyl ketone in a Diels-Alder cycloaddition.

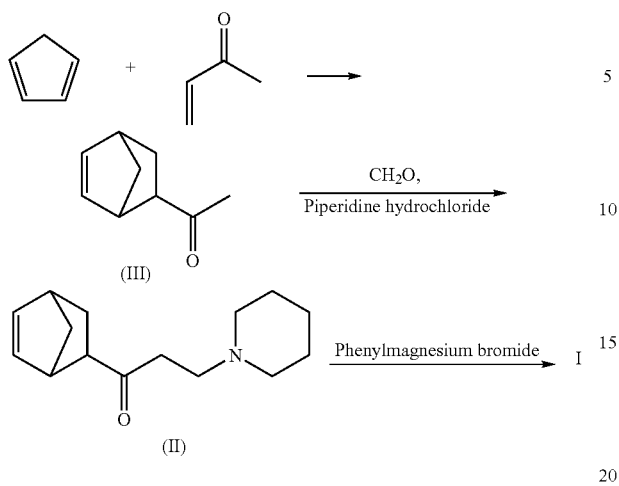

Neither DE 1 005 067 nor U.S. Pat. No. 2,789,110 disclose whether the amino alcohol I obtained in this way is a mixture of isomers or a pure isomer.

The precursor for preparing the propanol, 1-(bicyclo[2.2.1]hept-5-en-2-yl)-3-piperidino-1-propanone (II), can exist in two isomeric forms, as exo or as endo isomer (II-exo, II-endo), and only the exo form is able to afford biperiden in the abovementioned reaction with a phenylmagnesium halide.

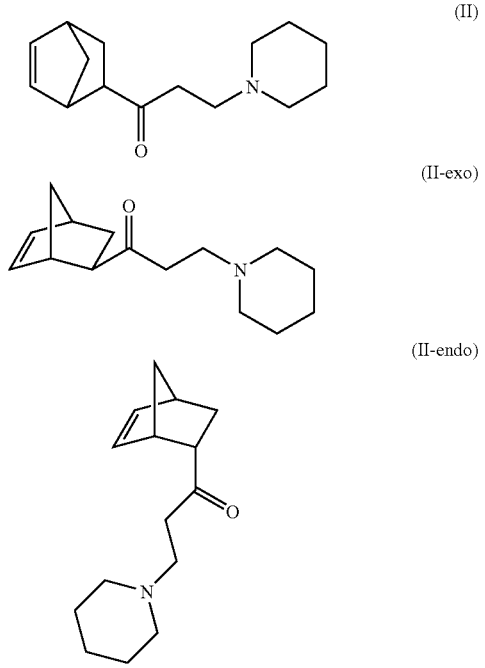

The structural formulae of II-exo and of II-endo show for the sake of simplicity in each case only one of two possible enantiomers of the exo isomer and endo isomer, respectively. However, the designation II-exo or II-endo relates hereinafter to the pair of enantiomers of the exo or endo form.

1-(Bicyclo[2.2.1]hept-5-en-2-yl)ethanone (III), the starting substance for synthesizing the propanone II, may also exist both as exo and as endo isomer (III-exo, III-endo) and, correspondingly, only reaction of the exo isomer leads in the subsequent steps to biperiden.

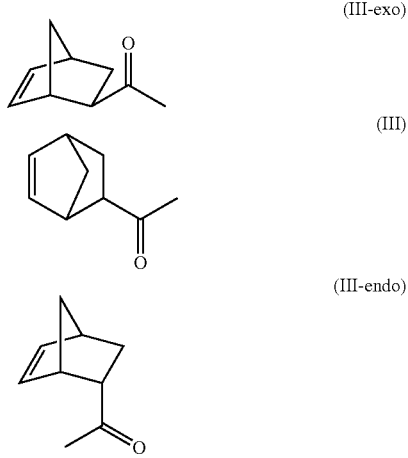

The structural formulae of III-exo and of III-endo show for the sake of simplicity in each case only one of two possible enantiomers of the exo isomer and endo isomer, respectively. However, the designation III-exo or III-endo relates hereinafter to the pair of enantiomers of the exo or endo form.

It is not possible to infer any information about the configuration of the precursors III and intermediates II employed in any of the abovementioned publications.

It is known that 1-(bicyclo[2.2.1]hept-5-en-2-yl)ethanone (III) is obtained from the cycloaddition in an exo/endo ratio of 1:4 (e.g. R. Breslow, U. Maitra, Tetrahedron Letters, 1984, 25, 1239). Since the prior art mentioned at the outset makes no statements at all about the stereochemistry of the ethanone III, it must be assumed that the ethanone III was employed in this ratio of isomers to prepare the amino alcohol I.

The preparation of exo-1-(bicyclo[2.2.1]hept-5-en-2-yl)ethanone (III-exo) was described in 1965 by J. G. Dinwiddie and S. P. McManus (J. Org. Chem., 1965, 30, 766). This entails exo/endo mixtures of 1-(bicyclo[2.2.1]hept-5-en-2-yl)ethanone (III) in which the endo content predominates being heated in methanol in the presence of sodium methanolate and isomerizing to mixtures with an exo content of about 70%. It is possible to obtain from this by fractional distillation and, where appropriate, redistillation of the distillate exo-1-(bicyclo[2.2.1]hept-5-en-2-yl)ethanone (III-exo) with a purity of up to 95%.

Experiments by the applicant has shown that even on use of pure exo ethanone III-exo as starting material in the Mannich reaction there is always production of an exo/endo mixture of the propanone II. This disadvantage is in relation to the yield of pure biperiden (Ia) in the subsequent reaction of the propanone II to give the propanol I. Pure biperiden means the biperiden (Ia) with a purity of at least 99.0%, as is generally necessary for pharmaceutical applications.

It is an object of the present invention to provide a method for producing biperiden which provides the latter in a higher yield, this method including a method for producing exo propanone II-exo of maximum isomeric purity. Exo propanone II-exo is intended to mean a propanone II which is at least 96%, preferably at least 97%, and particularly preferably at least 98% composed of the exo isomer II-exo. Biperiden is intended to mean a substance of the structural formula Ia.

It has been possible to achieve the object by a method for producing biperiden (Ia) by reacting exo-1-(bicyclo[2.2.1]hept-5-en-2-yl)-3-piperidino-1-propanone (II-exo) with a phenyl-magnesium compound, characterized in that the production of the exo-1-(bicyclo[2.2.1]hept-5-en-2-yl)-3-piperidino-1-propanone (II-exo) comprises the following steps:

a) conversion of exo-1-(bicyclo[2.2.1]hept-5-en-2-yl)ethanone (III-exo) into an exo silyl enol ether IV

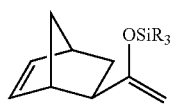

(IV)

in which R may be identical or different and is an alkyl group or a cycloalkyl group, and b) reaction of the exo silyl enol ether IV with an N-methylenepiperidinium compound.

The structural formula of the exo silyl enol ether IV shows for the sake of simplicity only one of two possible enantiomers. However, the term exo silyl enol ether IV refers hereinafter to the pair of enantiomers.

Exo-1-(bicyclo[2.2.1]hept-5-en-2-yl)ethanone (III-exo) is intended hereafter to mean an ethanone III which is at least 96%, preferably at least 97% and particularly preferably at least 98% composed of the exo isomer III-exo. A corresponding statement applies to the exo silyl enol ether IV.

The exo isomers employed in the method of the invention are, as already described for the exo ethanone III-exo, the exo propanone II-exo and for the exo silyl enol ether IV, pairs of enantiomers. In order to obtain biperiden (Ia), which is itself a racemate, racemic mixtures of enantiomers of the starting materials and of the intermediates are employed. However, the method of the invention can also be applied to pure enantiomers and to nonracemic mixtures of enantiomers.

The exo ethanone III-exo is converted into the corresponding exo silyl enol ether IV in general by first converting the exo ethanone III-exo with a base into the exo enolate V and then reacting the latter with a suitable silyl compound.

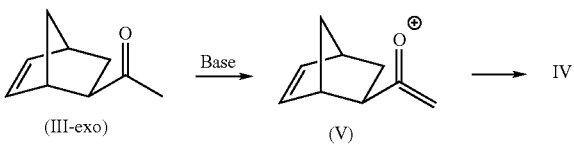

The structural formula of the exo enolate V shows for the sake of simplicity only one or two possible enantiomers. However, the term exo enolate V refers hereinafter to the pair of enantiomers.

Exo enolate V is intended to mean hereinafter an enolate V which is at least 96%, preferably at least 97% and particularly preferably at least 98% composed of the exo isomer.

Suitable silyl compounds for reaction with the exo enolate V are compounds of the general formula $R_3Si-X$ in which R has the aforementioned meanings, and X is a nucleophilically displaceable leaving group, preferably a halogen atom and in particular chlorine. In this connection, alkyl preferably has 1 to 4 carbon atoms, i.e. selected from methyl, ethyl, n-propyl, isopropyl, n-butyl, isobutyl, sec-butyl or tert-butyl. In this connection, cycloalkyl preferably has 5 to 8 carbon atoms, such as cyclopentyl, cyclohexyl, cycloheptyl or cyclooctyl. Particularly preferred silyl compounds ale the tri-$C_1$-$C_4$-alkylsilyl halides, and tri-$C_1$-$C_4$-alkylsilyl chlorides are particularly used. Trimethylsilyl chloride is particularly preferably employed.

The exo ethanone III-exo and the silyl compound are ordinarily employed in a molar ratio in the range from 1:1 to 1:2. The silyl compound is preferably employed in excess, preferably in an excess of from 10 to 100 mol %, in particular from 10 to 30 mol %, e.g. of 20 mol %.

The reaction generally takes place at a temperature in the range from −100 to 0° C., preferably from −85 to −10° C. and particularly preferably from −80 to −60° C., e.g. at −78° C.

The bases ordinarily used for the treatment of the exo ethanone III-exo with a base to convert into the exo enolate V are metal amides. Alkali metal amides are preferably used, in particular lithium amides. The amide nitrogen is preferably substituted once or twice. Suitable substituents on the amide nitrogen are $C_1$-$C_4$-alkyl radicals such as methyl, ethyl, n-propyl, isopropyl, n-butyl, sec-butyl or tert-butyl, also $C_5$-$C_8$-cycloalkyl radicals such as cyclopentyl, cyclohexyl, cycloheptyl or cyclooctyl which may in turn have 1 to 4 methyl groups, and tri-$C_1$-$C_4$-alkylsilyl radicals such as trimethylsilyl or triisopropylsilyl. The amide nitrogen may additionally be disubstituted in such a way that it forms part of a saturated 5- or 6-membered heterocycle which may in turn be substituted by 1, 2, 3 or 4 $C_1$-$C_4$-alkyl groups, especially methyl groups, such as, for example, in the amides of piperidine, 2,2,6,6-tetramethyl-piperidine or pyrrolidine. The amide nitrogen is preferably disubstituted. Lithium diisopropylamide is particularly preferably employed as base.

Reaction of the exo ethanone III-exo with the base generally takes place in a suitable solvent in a molar ratio of the exo ethanone III-exo to the base in the range of 1:1 to 1:1.5, preferably from 1:1 to 1:1.2 and particularly preferably virtually equimolar.

Reaction of the exo ethanone III-exo with the base is ordinarily carried out in an inert solvent. Solvents suitable for this purpose are $C_5$-$C_9$ aliphatic compounds such as n-hexane or n-heptane, aromatic compounds such as benzene, toluene, xylenes or ethylbenzene, aliphatic $C_4$-$C_8$ ethers such as diethyl ether, diisopropyl ether, tert-butyl methyl ether or 1,2-dimethoxyethane, alicyclic $C_4$-$C_6$ ethers such as tetrahydrofuran or dioxane or mixtures thereof. The solvents are ordinarily employed anhydrous, as usual for such reactions. In a specific embodiment of the method of the invention, a mixture of tetrahydrofuran, ethylbenzene and n-heptane is employed as solvent when lithium diisopropylamide is used as base.

Reaction of the exo ethanone III-exo with the base ordinarily takes place at a temperature in the range from −100° C. to 0° C., preferably from −85 to −10° C. and particularly preferably from −80 to −60° C., e.g. at −78° C. It is possible for the reaction to add the base to the exo ethanone III-exo or, conversely, to add the exo ethanone III-exo to the base, and the latter possibility is preferred. It is suitable for this purpose to add the exo ethanone III-exo to the solution of the base in one or more of the abovementioned solvents at the temperatures described above. The concentration of the base in the solution is normally from 0.1 to 10 mol/l, preferably 1 to 3 mol/l. The exo ethanone III-exo is generally added in portions; the exo ethanone III-exo is moreover added undiluted or dissolved in one or more of the abovementioned solvents, preferably in the same solvent(s) in which the base is dissolved, in a concentration of from 0.1 to 20 mol/l, preferably from 1 to 15 mol/l. However, the exo ethanone III-exo is preferably added in pure form. To complete the reaction, the mixture can be left in the temperature range defined above for from 10 minutes to, for example, 5 hours, preferably 30 minutes to one hour, during which it is preferably stirred.

To the reaction mixture which has been obtained in this way and which contains the exo enolate V, one of the organosilicon compounds described above is added, normally in situ, i.e. without previous isolation of the enolate, in the temperature range defined above. The silyl compound can be added all at once or, preferably, over a period of from 5 minutes up to several hours, in particular from 10 minutes up to one hour, undiluted or dissolved in one or more of the abovementioned solvents. The silyl compound is preferably added in pure form. On addition of solution, the concentration of the silyl compound is ordinarily from 0.1 to 20 mol/l, preferably 1 to 15 mol/l. To complete the reaction, the reaction mixture is ordinarily left for some time, e.g. from 1 to 5 hours, during which it is preferably stirred. It is moreover possible for the temperature of the mixture to be left at the abovementioned values or, preferably, allowed to reach room temperature, e.g. by removing the cooling apparatus Both the production of the exo enolate V and reaction thereof to give the exo silyl enol ether IV suitably take place under an inert gas atmosphere. Examples of suitable inert gases are nitrogen and the noble gases such as argon.

The reaction mixture is preferably worked up by aqueous extraction. The crude exo silyl enol ether IV obtained therefrom is purified where appropriate by distillation, preferably in vacuo. The exo silyl enol ether IV obtained in this way is novel and, is a valuable intermediate for producing biperiden (Ia), the present invention likewise relates thereto.

The subsequent reaction of the exo silyl enol ether IV with an N-methylenepiperidinium compound to give the exo propanone II-exo generally takes place in a suitable polar aprotic organic solvent. Suitable polar aprotic organic solvents include aliphatic $C_4$-$C_8$ ethers such as diethyl ether, diisopropyl ether or 1,2-dimethoxyethane, alicyclic $C_4$-$C_6$ ethers such as tetrahydro-furan or dioxane, chlorinated $C_1$-$C_2$ aliphatic compounds such as dichloromethane, carboxylic acid derivatives such as acetonitrile, N,N-dimethylformamide or N-alkylpyrrolidones, e.g. N-methyl-2-pyrrolidone, and sulfoxides such as dimethyl sulfoxide. N,N-Dimethylformamide or N-methyl-2-pyrrolidone is preferably used. The solvents are ordinarily employed anhydrous, as usual for reactions with N-methylenepiperidinium compounds.

The exo silyl enol ether IV and the N-methylenepiperidinium compound are preferably employed with a molar ratio of IV to N-methylenepiperidinium compound in the range from 1:1 to 1:2. The N-methylenepiperidinium compound is employed in particular in excess, e.g. in an excess of from 10 to 100 mol %, particulary preferably 20 to 70 mol %, e.g. 50 mol %, based on IV.

The exo silyl enol ether IV is preferably introduced into the solvent at a temperature in the range from −60 to 10° C., in particular from −40 to 0° C. and particularly preferably from −30 to −15° C. and then, at these temperatures, the N-methylenepiperidinium compound is added. The addition can take place in one portion or over a period of from 5 minutes up to several hours. To complete the reaction, the mixture is suitably left for some time, e.g. 15 minutes to 5 hours, during which it is preferably stirred. It is moreover possible to leave the mixture in the temperature range defined above or preferably allow it to reach room temperature.

It is, of course, also possible to add the exo silyl enol ether IV to the N-methylenepiperidinium compound, but addition of the N-methylenepiperidinium compound to the exo silyl enol ether IV is preferred.

The exo propanone II-exo is ordinarily isolated from the reaction mixture by aqueous extraction. For this purpose, the reaction mixture to which water has been added is first washed at a pH of from 2 to 6, preferably from 2 to 6, e.g. 3, for purification with a solvent of limited or zero miscibility with water. Suitable solvents of limited or zero miscibility with water include $C_5$-$C_6$ aliphatic compounds such as n-pentane or n-hexane, $C_5$-$C_6$ alicyclic compounds such as cyclohexane, aromatic compounds such as benzene, toluene or xylenes, aliphatic $C_4$-$C_8$ ethers such as dimethyl ether, tert-butyl methyl ether or diisopropyl ether or mixtures thereof. Aliphatic $C_4$-$C_8$ ethers such as diisopropyl ether are preferably used.

After the washing, the aqueous phase is adjusted to a pH of, ordinarily, from 7.5 to 12, preferably from 9 to 11, e.g. 10, with a suitable base, preferably in the form of the aqueous solution thereof, and extracted, where appropriate several times, with one of the abovementioned solvents. Suitable bases include alkali metal or alkaline earth metal hydroxides or alkali metal carbonates. Alkali metal hydroxides or their aqueous solutions are preferably used, in particular potassium hydroxide or potassium hydroxide solution, or sodium hydroxide or sodium hydroxide solution. Removal of the solvent from the alkaline extract(s), which takes place for example by distillation, preferably under reduced pressure, results in a propanone II which is at least 96% composed of the iso isomer II-exo. The propanone II thus has an exci/endo ratio of at least 24:1. It has not to date been possible to produce a propanone II with such a high proportion of exo isomer, and it is thus novel and the present invention likewise relates thereto.

The proportion of the exo isomer II-exo in the propanone II depends virtually exclusively on the degree of purity of the exo ethanone III-exo employed. Thus, use of an ethanone III with an exo proportion of 100% results in a propanone II with an exo proportion of about 100%.

In the reaction according to the invention of the exo ethanone III-exo to give the propanone II, the latter is obtained not only in the form of exo isomer III-exo, without isomerization being observed, but also in the considerably larger yield compared with the conventional procedure The term exo-1-(bicyclo[2.2.1]hept-5-en-2-yl)-3-piperidino-1-propanone (II-exo) means here and hereinafter a propanone II which is from 96 to 100% composed of the exo propanone II-exo.

The exo-1-(bicyclo[2.2.1]hept-5-en-2-yl)-3-piperidino-1-propanone (II-exo) produced according to the invention is subsequently reacted with a phenylmagnesium compound in a Grignard reaction to produce the biperiden. Preferred phenylmagnesium compounds are diphenylmagnesium and particularly preferably phenylmagnesium compound of the general formula

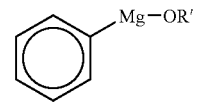

where R' is $C_1$-$C_4$-alkyl, such as methyl, ethyl, n-propyl, isopropyl or n-butyl, $C_4$-$C_6$-cycloalkyl, such as cyclohexyl, $C_4$-$C_6$-cycloalkyl-$C_1$-$C_4$-alkyl, such as 2-cyclohexylethyl, phenyl-$C_1$-$C_4$-alkyl, such as benzyl, 2-phenylethyl or 3-phenylpropyl, substituted phenyl-$C_1$-$C_4$-alkyl, such as 3,4-(methylenedioxy)benzyl, heteroaryl, such as 8-quinolyl, heteroaryl-$C_1$-$C_4$-alkyl, such as furfuryl, 2-thienylmethyl or 2-(2-thienyl)ethyl, or benzhydryl. The reaction is normally carried out in a solvent suitable for Grignard reactions. The phenylmagnesium compound of the formula depicted above is referred to hereinafter as phenylmagnesium alkoxide.

Suitable solvents are aromatic compounds such as benzene, toluene, or xylenes, acyclic or cyclic ethers having 4 to 6 carbon atoms, mixtures thereof or mixtures of them with aliphatic or alicyclic hydrocarbons such as n-hexane or cyclohexane. Examples of suitable alicyclic ethers are diethyl ether and tert-butyl methyl ether, and examples of suitable cyclic ethers are tetrahydrofuran and dioxane. Diethyl ether, tetrahydrofuran or dioxane or mixtures thereof are preferably used. The solvents are usually employed anhydrous, as normal for Grignard reactions.

The phenylmagnesium alkoxide is prepared in a generally known manner, eg. by reacting diphenylmagnesium with an alcohol of the general formula R'OH in which R' is as defined above. Diphenyl-magnesium and the alcohol are for this purpose reacted in a molar ratio in the range from 1:0.9 to 1:1.5, preferably in the range from 1:1 to 1:1.2 and particularly preferably approximately equimolar. Diphenylmagnesium, which is usually generated in situ as described hereinafter, is ordinarily introduced into one of the abovementioned solvents suitable for Grignard reactions, and the alcohol is normally added in portions over a period of from 5 minutes up to about one hour at a temperature of from 0 to 80° C., preferably from 0 to 50° C. and particularly preferably from 0 to 40° C. After the addition is complete, the mixture can be left, or preferably stirred, in the same temperature range for 15 minutes to 2 hours, preferably 15 minutes to one hour, until the reaction is complete.

The diphenylmagnesium employed in the method of the invention is produced in a manner known per se. For example, dioxane can be added to a phenylmagnesium halide, e.g. phenylmagnesium chloride, in a suitable solvent, thus shifting the Schlenk equilibrium to result in diphenylmagnesium and the corresponding magnesium halide-dioxane complex. The latter usually precipitates, but is preferably not removed from the solution. Suitable solvents are generally acyclic and cyclic ethers preferably having 4 to 6 C atoms or mixtures thereof with aliphatic, alicyclic or aromatic hydrocarbons. Examples of suitable acyclic ethers are diethyl ether and tert-butyl methyl ether, and a suitable cyclic ether is tetrahydrofuran. The suitable aliphatic and alicyclic hydrocarbons include in particular n-hexane and cyclohexane, and examples of suitable aromatic hydrocarbons are benzene, toluene and xylenes.

Dioxane is ordinarily employed at least equimolar in relation to the phenylmagnesium halide. If diphenylmagnesium is to be used as phenylmagnesium compound, then dioxane is preferably employed in excess, for example in an excess of from 50 to 500 mol %, in particular from 100 to 300 mol % and specifically of from 100 to 200 mol %. If diphenylmagnesium is first to be converted into the phenylmagnesium alkoxide, preferably dioxane and the phenylmagnesium halide are erployed in a molar ratio in the range from 1:1 to 1.5:1, in particular 1:1 to 1.2:1 and particularly preferably approximately equimolar.

The dioxane is added to the s;olution of the phenylmagnesium halide usually at a temperature in the range from −20 to 60° C., preferably in the range from −10 to 40° C.

The mixture obtained after addition of the dioxane is normally left for from 15 minutes to 2 hours, preferably 20 minutes to one hour, in the temperature range mentioned for the addition of the dioxane, before it is employed in the method of the invention.

Both the preparation of diphenylmagnesium, the reaction to give the phenylmagnesium alkoxide and the Grignard reaction with the exo propanone II-exo are suitably carried out under an inert gas atmosphere. Examples of suitable inert gases are nitrogen and the noble gases such as argon, and mixtures thereof.

In the Grignard reaction of the exo propanone II-exo with the phenyl-magnesium compound, ordinarily the phenylmagnesium compound and the exo propanol II-exo are employed in a molar ratio in the range from 0.8:1 to 3:1, preferably in the range from 0.8:1 to 2:1 and in particular in the range from 0.8:1 to 1.5:1. Where diphenylmagnesium or the phenylmagnesium alkoxide is used, the phenylmagnesium compound and the exo propanone II-exo are particularly preferably employed in a molar ratio in the range from 1:1 to 1.3:1.

Ordinarily, the exo propanone II-exo is added to the phenylmagnesium compound in the form of a solution in one of the abovementioned organic solvents suitable for Grignard reactions at a temperature in the range from −20° C. to the boiling point, preferably in the range from −10° C. to 90° C. and particularly preferably in the range from 0° C. to 70° C. The phenylmagnesium compound is moreover ordinarily employed in a concentration in the range from 0.1 to 10 mol/l, preferably in the range from 0.1 to 3 mol/l and particularly preferably in the range from 0.2 to 2 mol/l.

The exo propanone II-exo can be added in one portion or, preferably, over a period of from a few minutes to several hours, e.g. 5 minutes to 5 hours. The exo propanone II-exo is added either in the form of a solution in one of the abovementioned inert solvents suitable for Grignard reactions or, preferably, in pure form. When added as solution, the concentration of the exo propanbne II-exo is ordinarily from 0.1 to 20 mol/l, preferably 1 to 15 mol/l. To complete the reaction, the reaction mixture is normally left at a temperature in the range from −20° C. to the boiling point of the reaction mixture, preferably in the range from −10° C. to 90° C. and particularly preferably in the range from 10° C. to 80° C. for from 15 minutes to 5 hours, specifically 30 minutes to 2 hours, during which it is preferably stirred to improve mixing. Workup is, as usual for Grignard reactions, by aqueous extraction, e.g. by quenching the reaction mixture with water, an aqueous ammonium chloride solution or an acidic aqueous solution, with the pH of the resulting mixture in the latteir case subsequently being made alkaline, extracting the quenched mixture, where appropriate after removal of an organic phase, with a water-immiscible solvent suitable for dissolving the product, and removing the solvent from the extract or from the extract combined with the organic phase. Examples of suitable solvents are aromatic compounds such as benzene or toluene, the abovementioned acyclic ethers, esters such as ethyl acetate or chlorine-containing aliphatic compounds such as dichloromethane or trichloromethane.

The crude product obtained from the reaction according to the invention of the exo propanone II-exo with diphenylmagnesium or with a phenylmagnesium alkoxide consists essentially of the two diastereomeric pairs of exo enantiomers Ia and Ib of 1-(bicyclo[2.2.1]hept-5-en-2-yl)-1-phenyl-3-piperidino-1-propanol (I), with the pair of enantiomers Ia (biperiden) forming by far the major quantity. The ratio of biperiden (Ia) to the pair of enantiomers Ib determined by gas chromatography is frequently about 4:1.

The biperiden (Ia) is isolated from the mixture of diastereomers by dissolving the latter with heating, preferably at a temperature of from 40 to 80° C., in particular from 50 to 70° C., in a mixture of water and a polar, water-miscible organic solvent. Suitable solvents are $C_1$-$C_3$-alkanols, i.e. methanol, ethanol, n-propanol and isopropanol. Aqueous isopropanol is preferably used, particularly preferably 70 to 95% isopropanol and especially 90% isopropanol. The percentage data given here and hereinafter in relation to the isopropanol content are based on the volume of the isopropanol relative to the total volume of the water-containing solvent. HCl is added to this solution, for example in the form of a solution of hydrogen chloride in an organic solvent, preferably in one of the $C_1$-$C_3$-alkanols mentioned, with preference in isopropanol, or in the form of hydrochloric acid. HCl is employed at least equimolar in relation to the mixture of the diastereomeic amino alcohols, preferably in an excess of from 5 to 50 mol % and particularly preferably from 5 to 20 mol %. The addition preferably takes place at elevated temperature, e.g. at 40 to 80° C. and in particular at 50 to 70° C. To complete the reaction after addition is complete, the reaction mixture is left at a temperature of from 50° C. up to the boiling point of the reaction mixture for 0.5 to 3 hours, preferably while stirring. In a preferred embodiment, the reaction mixture is stirred at 55 to 65° C. for the first two thirds of the time and then stirred at the reflux temperature for one third of the time. The reaction mixture is then cooled to a temperature in the range from 0 to 30° C., where appropriate stirred in this temperature range for up to several hours, e.g. up to 10 hours, preferably up to 5 hours, and then the hydrochloride which has formed is removed from the solution in a conventional way.

For further purification of the hydrochloride, it is generally taken up wet or dry in water and a sufficient amount of one or more polar dialkyl ethers of limited or zero miscibility with water and having 4 to 8 C atoms, such as diethyl ether, tert-butyl methyl ether and especially diisopropyl ether, and a suitable base is added to the mixture. Suitable amounts of organic solvents are, for example, from 4 to 10 ml of solvent per gram of dry hydrochloride. Water and organic solvent are preferably employed in a ratio in the range from 1:2 to 1:5 by volume.

Suitable bases are alkali metal and alkaline earth metal hydroxides, and alkali metal carbonates; sodium or potassium hydroxide or their aqueous solutions are particularly preferably used, sodium hydroxide or sodium hydroxide solution are especially used. However, it is also possible to use water-soluble organic bases, for example amines having aliphatic substituents and 2 to 8 C atoms. The base is employed at least equimolar, preferably in excess, in particular in an excess of from 5 to 15 mol % based on the hydrochloride.

The reaction with the base preferably takes place at elevated temperature. For this purpose, before, during or, preferably, after addition of the base the mixture is heated to a temperature in the range above 25° C. up to the boiling point of the reaction mixture, preferably in the range from 30 to 70° C., and when diisopropyl ether is used as dialkyl ether preferably in the range from 40 to 65° C., in particular from 55 to 60° C. This generally results in two clear phases which are separated at elevated temperature, in the case where diisopropyl ether is used as dialkyl ether in the abovementioned temperature range. The organic phase is washed with water at elevated temperature, in the case where diisopropyl ether is used as dialkyl ether in the abovementioned temperature range, and then concentrated preferably under atmospheric pressure by removing the solvent until the weight/volume ratio of the product to the solvent is in the range from 1:2 to 1:6, preferably from 1:3 to 1:4.5. When the mixture is cooled to room temperature or below, but preferably not below −10° C., pure biperiden (Ia) crystallizes out and is isolated by conventional methods for isolating solids, e.g. filtering off the solid or decanting off the mother liquor.

It was possible by the use according to the invention of a propanone II having a proportion of at least 96% of exo to increase the yield of biperiden (Ia) considerably, especially in combination with the workup described above Biperiden (Ia) can then be converted with a pharmacologically acceptable acid in a conventional manner into its acid addition salt. Examples of suitable acids are hydrohalic acids, in particular hydrogen chloride or hydrochloric acid, and organic mono- or dicarboxylic acids such as acetic acid, oxalic acid, maleic acid, fumaric acid, lactic acid, tartaric acid, adipic acid or benzoic acid, also phosphoric acid and sulfuric acid, and the acids mentioned in "Fortschritte der Arzneimittelforschung, volume 10, pages 224 et seq., Birkhäuser Verlag, Basle, Stuttgart, 966". Biperiden (Ia) is normally marketed as hydrochloride.

The exo-1-(bicyclo[2.2.1]hept-5-en-2-yl)ethanone (III-exo) used to prepare the exo-1-(bicyclo[2.2.1]hept-5-en-2-yl)-3-piperidino-1-propanone II-exo is obtained by a Diels-Alder cycloaddition reaction of cyclopentadiene and methyl vinyl ketone. A particularly preferred method for preparing III, which affords a product with a high content of III-exo, is described in the German patent application 10124450.9, the disclosure of which is incorporated herein by reference. The cycloaddition of cyclopentadiene and methyl vinyl ketone can be carried out in a solvent conventional for such reactions, such as diethyl ether, benzene, toluene or xylene or else without solvent. It is preferred to use no solvent. Cyclopentadiene and methyl vinyl ketone are normally employed in a molar ratio in the range from 3.0:1 to 0.5:1. They are preferably reacted equimolar or with cyclopentadiene in excess, with the excess preferably being 50 to 150 mol %.

The reaction is usually carried out at a temperature in the range from 0 to 60° C., preferably in the range from 10 to 40° C.

Low-boiling constituents, usually unreacted precursors, are usually removed following the cycloaddition by distillation under reduced pressure, preferably under 1 to 150 mbar. The remaining mixture, which consists of about 20% exo- and about 80% endo-1-(bicyclo[2.2.1]hept-5-en-2-yl)ethanone, is reacted with an alkali metal $C_1$-$C_4$-alcoholate. The amount of alkali metal alcoholate is usually from 0.1 to 5% by weight, preferably from 0.2 to 2% by weight, based on the total weight of the mixture. Sodium methanolate is preferably used. The temperature necessary for isomerization of the ethanone III is usually in the range from 50 to 110° C., preferably in the range from 60 to 100° C. For this purpose, the mixture is often heated under reduced pressure to reflux, preferably under a pressure of from 1 to 100 mbar and in particular under a pressure of from 5 to 50 mbar. These conditions are usually applied for from 10 minutes to hours, in particular 20 minutes to 3 hours and specifically 0.5 hours to 2 hours, and then fractional distillation of the resulting mixture is started, preferably distilling out the exo isomer of III. It is assumed that removal of the exo isomer from the equilibrium promotes isomerization of the endo ethanone to the exo form. The fractional distillation normally takes place through a column under reduced pressure, preferably in the range from 1 to 100 mbar, in particular from 1 to 50 and specifically from 1 to 20 mbar. The distillation temperature (distillate temperature) is preferably adjusted to from 50 to 100° C. and specifically to 50 to 80° C. In this way, exo-1-(bicyclo[2.2.1]-hept-5-en-2-yl)ethanone (III-exo) is obtained in a purity which is at least 96%.

Redistillation of the distillate results in purities of up to 100%. Exo ethanone III-exo with a purity of at least 96% is used in the method of the invention.

The following examples serve to illustrate the invention but are not to be understood as restrictive.

EXAMPLE

1. Preparation of the Starting Material 1.1 exo-1-(Bicyclo[2.2.1]hept-5-en-2-yl)ethanone (III-exo)

198.3 g of cyclopentadiene were rapidly added to 210.3 g of methyl vinyl ketone. After the addition was complete, the reaction solution was stirred at room temperature for one hour and then unreacted precursor was removed by distillation at a temperature of 58° C. and a pressure of 20 mbar. The residue from evaporation, mainly consisting of a mixture of the exo and the endo form of 1-(bicyclo[2.2.1]hept-5-en-2-yl)ethanone (III) in the ratio of 1:4, was heated to reflux with 5 g of sodium methanolate under a pressure of from 10 to 20 mbar for one hour. The reaction mixture was then distilled through a column at a temperature of 75° C. and a pressure of 20 mbar. This resulted in 298.3 g (73% of theory) of exo-1-(bicyclo[2.2.1]hept-5-en-2-yl)ethanone (III-exo) in the form of a pale yellowish oil.

1.2 exo-1-(Bicyclo[2.2.1]hept-5-en-2-yl)-3-piperidino-1-propanone (II-exo)

1.2.1 Preparation of the trimethylsilyl enol ether of the exo ethanone III-exo exo-({1-[bicyclo[2.2.1]hept-5-en-2-yl]vinyl}oxy)(trimethyl)silane (IV with R=methyl)

68.1 g of exo-1-(bicyclo[2.2.1]hept-5-en-2-yl)ethanone (III-exo), obtained as in example 1.1, were added dropwise over the course of 30 minutes to 250 ml of a 2M lithium diisopropylamide solution in tetrahydrofuran/ethylbenzene/n-heptane at −78° C. The mixture was stirred at −78° C. for a further hour. Then, at −78° C., 67.9 g of trimethylsilyl chloride were rapidly added dropwise. The cooling bath was removed and the solution was thawed to room temperature over the course of about 1.5 hours. the precipitate which had formed was filtered off with suction and washed with 100 ml of n-hexane. The combined filtrates were extracted with 250 ml of cold saturated aqueous sodium bicarbonate solution, and the phases were separated. The aqueous phase was then extracted three times with 100 ml of n-hexane each time. The three organic extracts were added to the combined filtrates, and the organic phase obtained in this way was dried over sodium sulfate. The solvent was removed and the resulting crude product was purified by distillation at 95° C./20 mbar. The distillate obtained was 83.4 g of exo-({1-[bicyclo[2.2.1]hept-5-en-2-yl]vinyl}oxy)-(trimethyl)silane (IV, R=methyl) in the form of a colorless oil; which is 80% of theory.

1.2.2 Preparation of exo-1-(bicyclo[2.2.1]hept-5-en-2-yl)-3-piperidino-1-propanone (II-exo)

83.4 g of exo-({1-[bicyclo[2.2.1]hept-5-en-2-yl]vinyl}oxy)-(trimethyl)silane (IV, R=methyl), obtained as in example 1.2.1, were introduced into 50 ml of N,N-dimethylformamide at −25° C. Subsequently, 73.5 g of N-methylenepiperidinium chloride were added, and the cooling bath was removed. The reaction mixture was stirred for 30 minutes and then added to 250 ml of cold water. The pH was adjusted to about 3 with dilute hydrochloric acid, and the solution was extracted three times with 75 ml of diisopropyl ether each time. The organic extracts were discarded. The aqueous phase was then adjusted to a pH of 10 with 50% concentrated sodium hydroxide solution and extracted three times with 75 ml of diisopropyl ether each time. The combined organic extracts were dried over sodium sulfate, and the solvent was removed in vacuo. This resulted in 91.5 g of exo-1-(bicyclo[2.2.1]hept-5-en-2-yl)-3-piperidino-1-propanone (II-exo) in the form of a colorless oil; which is 98% of theory.

2. Preparation of Biperiden (Ia)

103.1 g of dioxane were added dropwise at 0° C. to 640 g of a 25% strength solution of phenylmagnesium chloride in tetrahydrofuran, during which a white precipitate formed. After stirring while cooling in an ice bath for 30 minutes, 71.5 g of 2-phenylethanol were added to the mixture. After stirring while cooling in an ice bath for a further 30 minutes, 91.5 g of exo-1-(bicyclo[2.2.1]hept-5-en-2-yl)-3-piperidino-1-propanone (II-exo), obtained as in example 1.2.2, were added while cooling in an ice bath. After the addition was complete, the ice bath was removed and the reaction mixture was stirred without cooling for a further hour. The mixture was then added slowly to 750 ml of ice-cold water. This was followed by extraction three times with 100 ml of toluene each time. The combined extracts were dried over sodium sulfate and evaporated in a rotary evaporator. The residue from evaporation—155.5 g of a mixture which consisted essentially of forms Ia and Ib of 1-(bicyclo[2.2.1]hept-5-en-2-yl)-1-phenyl-3-piperidino-1-propanol (I) in the ratio (GC) 4:1—was dissolved in 750 ml of isopropanol at the reflux temperature, 200 ml of water were added to the solution, and the 25 mixture was cooled to 60° C. At this temperature, 78 ml of 5M hydrochloric acid were added. Addition of acid was followed by stirring at 60° C. for one hour and then at the reflux temperature for half an hour. After cooling to room temperature, the crystals which had separated out were removed, washed with 150 ml of isopropanol and dried in vacuo at 70° C. The hydrochloride (66.5 g) obtained in this way was stirred in 375 ml of diisopropyl ether and 100 ml of water while 78 ml of 5M sodium hydroxide solution were added. The mixture was stirred at the reflux temperature for minutes, the aqueous phase was separated off hot, and 150 ml of solvent were removed from the organic phase by distillation under atmospheric pressure. The residue from distillation was allowed to cool to room temperature while stirring. After cooling for a further hour in an ice bath, the crystals which had separated out were removed, washed with 20 ml of diisopropyl ether and dried in vacuo at 40° C. 53.5 g of biperiden (Ia) were obtained as colorless crystals of melting point 112 to 114° C. (Ullmanns Enzyklopädie der techn. Chemie, 4th edition, volume 21, Verlag Chemie, 1982, page 627: 112-114° C.); which is 44% of theory.

3. Preparation of Biperiden Hydrochloride 93.4 g of biperiden (Ia) were dissolved in 1 000 ml of isopropanol by heating to the reflux temperature. The solution was filtered hot, and the filter was washed with 100 ml of isopropanol. 65 ml of 5M hydrochloric acid were added to the combined filtrates at 75° C. The mixture was then heated to reflux for 15 minutes. After cooling to room temperature and stirring at this temperature for one hour, the precipitated solid was filtered off with suction, washed twice with 50 ml of isopropanol each time and dried in vacuo at 70° C. 103.2 g of biperiden hydrochloride were obtained in the form of colorless crystals of melting point 278 to 280° C. (Ullmanns Enzyklopädie der techn. Chemie, 4th edition, volume 21, Verlag Chemie, 1982, page 627: 278-280° C.); which is 98.9% of theory.

We claim:

1. A method for producing biperiden by reacting exo-l-(bicyclo[2.2.1]hept-5-en-2-yl)-3-piperidino-l-propanone with a phenylmagnesium compound, characterized in that the production of the exo-1-(bicyclo(2.2.1]hept-5-en-2-yl)-3-piperidino-l-propanone comprises the following steps:

a) conversion of exo-1-(bicyclo[2.2.1]hept-5-en-2-yl)-ethanone into an exo silyl enol ether IV

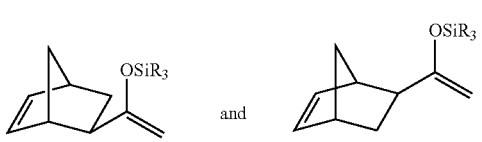

(IV)

in which $R_3$ may be identical or different and is alkyl or cycloalkyl, and b) reaction of the exo silyl enol ether with an N-methylenepiperidinium compound.

2. The method of claim 1, characterized in that in step a) the exo ethanone is converted with a metal amide as base into the exo metal enolate V

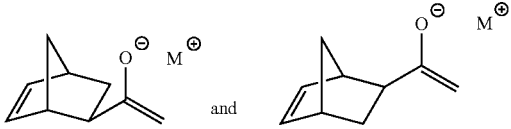

(V)

and the latter is then converted with an organosilicon compound of the formula $R_3Si-X$, in which $R_3$ has the aforementioned meaning, and X is a halogen atom, into the exo silyl enol ether IV.

3. The method of claim 2, characterized in that an alkali metal amide is used as the metal amide.

4. The method of claim 3, characterized in that a lithium amide is used as the alkali metal amide.

5. The method of claim 4, characterized in that lithium diisopropylamide is used as the lithium amide.

6. The method of claim 2, characterized in that the exo ethanone and the metal amide are employed in a molar ratio of exo ethanone to metal amide in the range from 1:1 to 1:1.5.

7. The method of claim 1, characterized in that exo-1-(bicyclo [2.2.1]hept-5-en2-yl)ethanone is converted into the exo trimethylsilyl enol ether with R = methyl.

8. The method of claim 7, characterized in that trimethylsilyl chloride is used in step a).

9. The method of claim 1, characterized in that step a) is carried out at a temperature in the range from -100 to 0° C.

10. The method of claim 1, characterized in that methylenepiperidinium chloride is used in step b).

11. The method of claim 10, characterized in that the N-methylenepiperidinium compound is reacted with the exo silyl enol ether in step b) in a molar ratio in the range from 1:1 to 2:1.

12. The method of claim 1, characterized in that step b) is carried out at a temperature in the range from -60 to 10° C.

13. The method of claim 1, characterized in that the reaction mixture resulting in step b) is converted into an aqueous solution, and the latter is washed at a pH not exceeding 6 with a solvent of limited or zero miscibility with water, the resulting raffinate is extracted at a pH of at least 7.5 with a solvent of limited or zero miscibility with water, and the solvent is removed from the extract, resulting in exo-1-(bicyclo[2.2.1]hept-5-en-2-yl)-3-piperidino-1-propanone.

14. The method of claim 1, characterized in that the phenylmagnesium, compound used is diphenylmagnesium or a phenylmagnesium. compound of the general formula

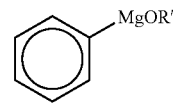

where R' is $C_1$-$C_4$-alkyl, $C_4$-$C_6$-cycloalkyl, $C_4$-$C_6$-cycloalkyl-$C_1$-$C_4$-alkyl, phenyl-$C_1$-$C_4$alkyl, substituted phenyl-$C_1$-$C_4$-alkyl, heteroaryl, heteroaryl-$C_1C_4$-alkyl or benzhydryl.

15. The method of claim 1, characterized in that to isolate biperiden from the reaction of the exo-1-(bicyclo[2.2.1]hept-5-en-2-yl)-3-piperidino-1-propanoe with the phenylmagnesium compound, the mixture of diastereomeric 1-(bicyclo-[2.2.1]hept-5-en-2-yl)-3-piperidino-1-propanols formed thereby is converted in aqueous isopropanol into the hydrochloride which is isolated, the hydrochloride is reacted with a base in water and diisopropyl ether, the aqueous phase is removed at elevated temperature, and part of the diisopropyl ether is removed from the organic phase and, after cooling, biperiden is isolated by removing the solid from the mother liquor.

16. The method as claimed in any of claim 1 or 15, wherein an exo-(1-[bicyclo(2.2.1]hept-5-en-2-yl]vinyl)oxy)silane of formula IV is produced as an intermediate compound, wherein

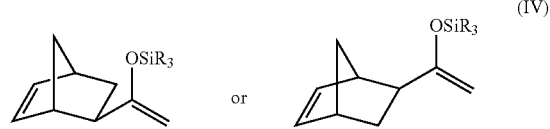

(IV)

$R_3$ is identical or different and is alkyl or cycloalkyl.

17. The method of claims 1, 15 or 16, wherein said method yields 1-(bicyclo[2.2.1]hept-5-en-2-yl)-3-piperidino-1-propanone with an exo/endo ratio of at least 24:1.

* * * * *